(12) United States Patent
Rüther et al.

(10) Patent No.: US 7,186,384 B2
(45) Date of Patent: Mar. 6, 2007

(54) SAMPLE ENTRY DEVICE FOR DELIVERING MEDICAL SAMPLES TO AN ANALYZER

(75) Inventors: Horst Rüther, Hart/Graz (AT); Michael Kraker, Hengsberg (AT)

(73) Assignee: Roche Diagnostics Corporation, Indianapolis, IN (US)

( * ) Notice: Subject to any disclaimer, the term of this patent is extended or adjusted under 35 U.S.C. 154(b) by 500 days.

(21) Appl. No.: 10/385,600

(22) Filed: Mar. 12, 2003

(65) Prior Publication Data

US 2003/0180193 A1  Sep. 25, 2003

(30) Foreign Application Priority Data

Mar. 19, 2002  (AT)  ............................. A 423/2002

(51) Int. Cl.
*B01L 3/02* (2006.01)
*G01N 1/00* (2006.01)
*G01M 1/14* (2006.01)

(52) U.S. Cl. .................... 422/103; 422/100; 422/58; 422/63; 422/64; 422/68.1; 73/864.81; 73/864.85; 73/864.87

(58) Field of Classification Search .......... 422/100, 422/104, 58, 63, 64, 68.1, 103; 436/180; 73/864.81, 864.85, 864.86, 864.87
See application file for complete search history.

(56) References Cited

U.S. PATENT DOCUMENTS

| | | | | |
|---|---|---|---|---|
| 3,550,452 A | * | 12/1970 | Halasz et al. ............. | 73/864.86 |
| 3,564,925 A | * | 2/1971 | Divelbiss et al. .......... | 73/864.85 |
| 4,478,095 A | * | 10/1984 | Bradley et al. ........... | 73/864.21 |
| 4,499,053 A | | 2/1985 | Jones | |
| 4,962,041 A | * | 10/1990 | Roginski ................... | 436/150 |
| 4,974,459 A | * | 12/1990 | Makela et al. ............ | 73/864.81 |
| 5,169,602 A | * | 12/1992 | Pang et al. ................ | 422/103 |
| 5,171,530 A | * | 12/1992 | Pennatto .................... | 422/63 |
| 5,391,499 A | | 2/1995 | Karkantis et al. | |
| 5,711,917 A | * | 1/1998 | Juranas et al. ............ | 422/99 |

(Continued)

FOREIGN PATENT DOCUMENTS

DE  3890175  4/1994

(Continued)

OTHER PUBLICATIONS

Patent Abstracts of Japan, vol. 010, No. 294 (P-504), Oct. 7, 1986 of JP 61-112967 to T. Nobuyoshi entitled "Specimen Introducing Apparatus".

*Primary Examiner*—Brian R. Gordon
(74) *Attorney, Agent, or Firm*—Dykema Gossett PLLC

(57) ABSTRACT

The invention relates to a sample entry device for delivering medical samples, preferably blood samples, from diverse sample containers to an analyzer, wherein sample transfer between sample intake and measuring cells of the analyzer taking place via gas-tight sample lines. According to the invention a fixed intake needle is provided at the entry side of the analyzer, which includes an elastic intake element that is axially slideable on the intake needle and has a conical intake opening. In addition, a holding element is provided, which is axially slideable parallel to the intake needle and can be shifted relative to the intake element. In a first position the holding element exposes the intake element and in a second position places a conical opening above the intake element to accommodate a syringe.

8 Claims, 3 Drawing Sheets

U.S. PATENT DOCUMENTS

| | | | |
|---|---|---|---|
| 5,753,105 A * | 5/1998 | Johnson | 210/86 |
| 5,945,070 A * | 8/1999 | Kath et al. | 422/101 |
| 5,997,819 A * | 12/1999 | Mougin et al. | 422/100 |
| 6,235,242 B1 * | 5/2001 | Small et al. | 422/78 |
| 6,395,235 B1 * | 5/2002 | Kilcoin et al. | 422/103 |
| 6,475,437 B1 * | 11/2002 | Gerstel et al. | 422/70 |
| 6,526,812 B2 * | 3/2003 | Martin et al. | 73/61.55 |
| 6,537,818 B2 * | 3/2003 | Richards et al. | 436/54 |
| 6,620,620 B1 * | 9/2003 | Anderson et al. | 436/55 |
| 6,833,113 B2 * | 12/2004 | Sentoh | 422/100 |
| 6,887,429 B1 * | 5/2005 | Marshall et al. | 422/81 |
| 2002/0110493 A1 * | 8/2002 | Dales et al. | 422/100 |
| 2002/0168778 A1 * | 11/2002 | Andrien et al. | 436/173 |
| 2002/0192113 A1 * | 12/2002 | Uffenheimer et al. | 422/67 |
| 2003/0100120 A1 * | 5/2003 | Wang et al. | 436/37 |
| 2004/0067165 A1 * | 4/2004 | Isobe et al. | 422/64 |

FOREIGN PATENT DOCUMENTS

| | | |
|---|---|---|
| EP | 0297082 | 12/1988 |
| EP | 0564439 | 10/1993 |

* cited by examiner

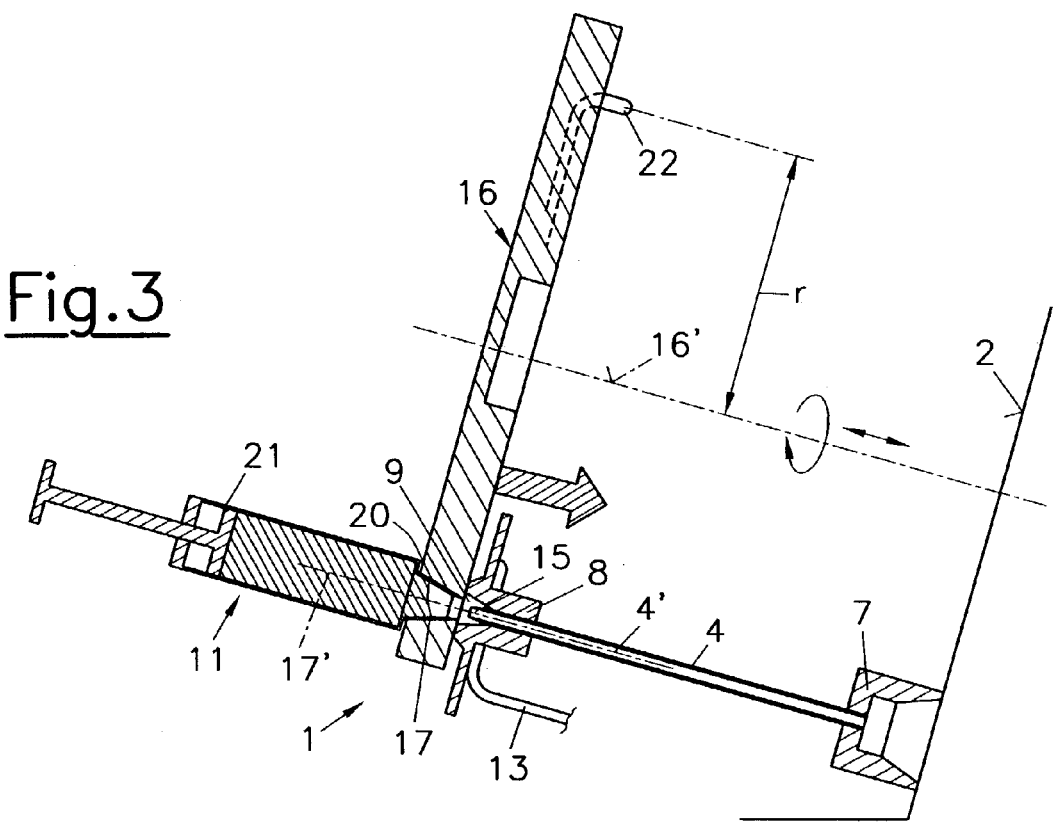
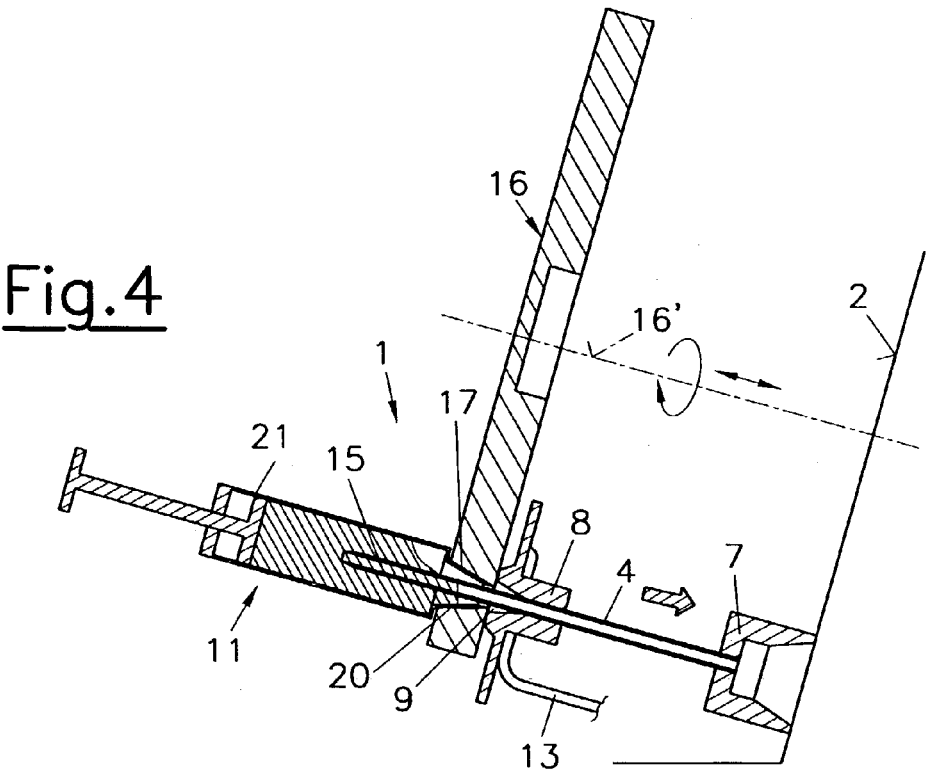

SAMPLE ENTRY DEVICE FOR DELIVERING MEDICAL SAMPLES TO AN ANALYZER

BACKGROUND OF THE INVENTION

The invention relates to a sample entry device for delivering medical samples, preferably blood samples, from diverse sample containers to an analyzer, sample transfer between sample intake and measuring cells of the analyzer being accomplished via gas-tight sample lines.

Such sample entry devices are known in the context of medical laboratories, where they are used in blood analysis and other fluid measuring processes. Equipment used for analysis often is configured for a special type of sample entry, such that sample entry may be effected only via a capillary or only by means of a syringe.

DESCRIPTION OF PRIOR ART

It has been found desirable before to develop a sample entry device, which will accept a syringe as well as a capillary for sample entry without necessitating complicated adaptations when switching from one entry means to another.

From EP 0 297 082 there is known a device for the analysis of body fluids, which is provided with a rotatable docking disk, which in its various positions may be connected to the feeder fitting of the sample feeding line of the analyzer. The sample entered via this docking disk may either be aspirated by means of a hose pump or injected into the sample input. The advantage of this sort of sample entry system lies in the fact that from the entry element of the analyzer onwards all sample, calibrating, and cleaning media use the same path inside the analyzer, thus establishing the same measurement conditions for all media in contrast to other known devices which use different entry ports for different sampling devices.

A sample entry system similar to that of EP 0 297 082 is described in DE 38 90 175 C1. In this sample entry system a distributor disk is provided, which is rotatable on an axle and includes a number of entry elements all having the same distance from the rotation axis and being connected to the respective fittings for the various media to be entered. The distributor disk is carried by a supporting axle in the housing of the analyzer, which latter also contains a control unit for the lifting and rotating motions of the distributor disk. In a certain rotatory position the distributor disk has a notch such that the sample entry opening for sample entry by means of a syringe or a pipette is uncovered. With the sample entry system described in DE 38 90 175 C1 the sample may be aspirated from a capillary or injected with the use of a syringe. In order to furnish a seal for the capillary or syringe to be inserted a conical entry opening is provided, which is directly connected via a rigid gas-tight tube to the measurement cells of the analyzer. This sample entry system is not suitable for a third method of sample entry frequently used in laboratories, i.e., for aspirating the sample from a syringe. With the arrangement described aspirating the sample from a syringe would create a partial vacuum inside the syringe and in the tube system of the analyzer, with the result that removal of the syringe would cause fragmentation of the sample and formation of air bubbles due to the sudden pressure change, thus making measurement more difficult and less reliable.

Similar problems with the aspiration of a sample from a syringe are also to be expected with a sample entry system known from EP 0 564 439 A2. For the input of cleaning and reference media a flap is provided in this case, which is tiltable about a fixed axle. In the closed position of the flap cleaning and reference media are fed into an elastic entry element of the analyzer, while in the open position the entry element may be accessed for aspiration from capillaries or for injection by means of a syringe.

Further known are sample entry systems which permit aspiration of the sample from a syringe. In a great number of such systems a tiltable intake needle is provided such that sample fluid may be aspirated into the analyzer from different sample containers in different positions of the needle. In this context reference is made to U.S. Pat. No. 4,499,053 A, which exhibits a relatively complicated lifting mechanism with a guide structure, aspiration of the sample being possible both from a capillary and a syringe. To this end the intake needle is provided with an intake element which is axially guided with its central bore on the intake needle by a guided link structure. By means of a handle on the guided link structure the intake needle may be tilted from a rest position, in which the needle is connected to a fitting for a cleaning solution, into various other positions in which the intake element, under control of the guide structure, assumes different positions along the axis of the intake needle.

In one of these lift positions the tip of the needle is fully exposed and may thus be dipped into an open sample container from which the sample may be aspirated. In another lift position the tip of the intake needle is positioned inside the central opening of the intake element in such a way that a sample capillary may be inserted into the remaining space of the central opening and held there. The sample may then be aspirated by the pump of the analyzer.

Finally a further lift position is provided in which the intake needle is essentially horizontal and the intake element exposes a short length of the needle tip. The cone of a syringe may then be placed over the needle tip and pressed against the outer face of the intake element, whereupon the sample may be injected into the analyzer. The following disadvantages are incurred by this variant: the syringe is not securely held by the intake device; pressing the syringe cone against the outer face of the intake element may not provide a sufficient seal; the sample may contaminate parts of the intake device.

A further grave disadvantage of the sample entry system according to U.S. Pat. No. 4,499,053 A is due to the fact that the tiltable intake needle is connected to the measuring cells by means of a flexible tube. This contradicts the requirement that moving parts and flexible gas-permeable tubes should be avoided between sample intake area and measuring cells.

Similar problems with flexible tube systems also occur with known devices where an intake needle is inserted into the interior of a syringe by means of a drive assembly.

In this context a sample entry system is described in U.S. Pat. No. 5,391,499 A, in which sample intake may be performed from two different sample containers, i.e., a syringe (see FIG. 1) or a sample capillary (FIG. 2). By means of a rotatable element in the sample intake area it will be possible to automatically infer from the diameter of the sample container whether a syringe or a sample capillary has been inserted into the intake opening, and thus to initiate an intake program suitable to the respective sample container used. The intake needle is either advanced in its longitudinal direction by means of a drive unit in order to penetrate into a syringe, or it is retracted to provide room for a sample capillary. Due to this longitudinal movement of the intake needle in U.S. Pat. No. 5,391,499 A a flexible (and thus gas-permeable) tube will be required to connect the intake needle to the measuring cell, which will entail the disadvantages described above. Another drawback of the sample entry system according to U.S. Pat. No. 5,391,499 A is that injection of the sample from a syringe will not be possible as the sample would seep from the lateral openings for supply and drainage of the cleaning solution.

It is further known to use different adaptors for the different types of sample containers, which adaptors are to be placed on or inserted into the intake element proper of the analyzer. This will significantly increase manipulatory effort and the risk of operational mistakes.

SUMMARY OF THE INVENTION

It is the object of the present invention to develop a sample entry device for medical samples, and preferably blood samples, in such a way that the samples may be entered from different sample containers in a mechanically simple manner, sample transport between entry device and the measuring cells of the analyzer taking place via rigid gas-tight lines.

According to the invention this object is achieved by providing a fixed intake needle at the entry side of the analyzer, which includes an elastic intake element that is axially slideable on the intake needle and has a conical intake opening, and by further providing a holding element which is axially slideable parallel to the intake needle and can be shifted relative to the intake element, and which in a first position exposes the intake element and in a second position places a conical opening above the intake element to accommodate a syringe. In the first position of the holding element, when the conical intake opening of the elastic intake element is exposed, the sample may either be aspirated from a capillary or injected from a syringe. In the second position, which, departing from the first position, is reached by a translatory or rotatory motion of the holding element, the holding element will take up the syringe, which is positioned above the intake needle and then slid over the intake needle by a subsequent lifting motion of the holding element. Thereafter, the sample can be aspirated from the interior of the syringe and the forming of a partial vacuum is avoided by ambient air entering through the annular gap between intake needle and the cone of the syringe.

In a first variant of the invention the holding element may be rotatably pivoted on an axle running parallel to the intake needle at a distance r, such that in a first rotational position the intake element is exposed while in a second rotational position the conical opening holding the syringe is positioned above the intake element.

In a second variant the holding element may be configured as a flap and may be rotatably pivoted on an axle which lies in a plane orthogonal to the intake needle, such that in a first position of the flap the intake element is exposed while in a second position of the flap the conical opening holding the syringe is positioned above the intake element.

It is provided by the invention that the analyzer have a driving unit for the lifting and rotatory motions, respectively the lifting and tilting motions, of the holding element, which unit is controlled by the processor unit of the analyzer.

In further development of the invention the proposal is put forward that the analyzer have a driving unit controlled by the processor unit of the analyzer, for the axial shifting of the elastic intake element from a first position near the tip of the intake needle to a second position in which the needle tip projects beyond the intake element, the driving unit being coupled to the elastic intake element via a linking element.

According to a particularly advantageous variant of the invention the holding element is configured as a distributor disk for the supply of calibrating, quality control and/or cleaning media, fittings for calibrating, quality control and/or cleaning media being provided in further rotational positions of the distributor disk at a distance r, which fittings may be brought into contact with the intake element.

BRIEF DESCRIPTION OF THE DRAWINGS

The invention will now be further described with reference to the enclosed drawings, wherein FIGS. 1 to 4 show, in part schematically, a first variant of a sample entry device for the input of medical samples into an analyzer according to the invention, in different operational states and in sectional representation.

DETAILED DESCRIPTION OF THE PREFERRED EMBODIMENTS

Figure 1:
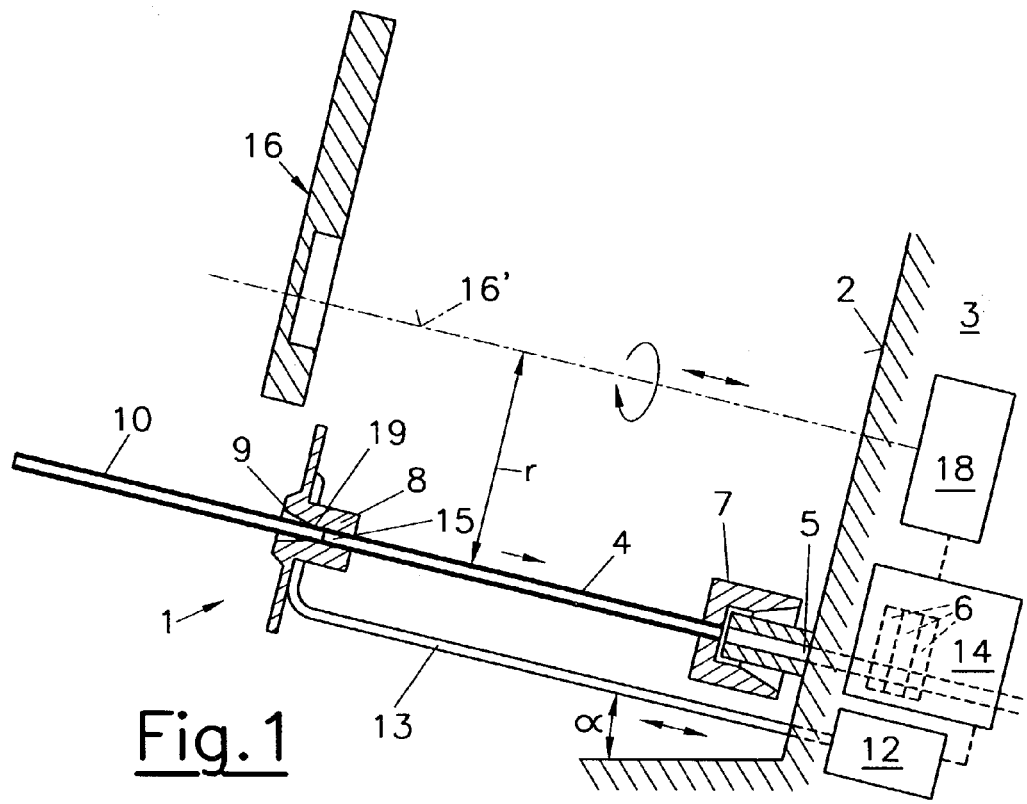

The variant of a sample entry device 1 shown in FIGS. 1 to 5 for an analyzer 3 represented by its front panel 2 comprises a rigid intake needle 4, e.g., a steel needle, which is connected via a rigid, gas-tight sample tube 5 to the measuring cells 6 in the analyzer 3. The intake needle 4 is provided with a coupling element 7 on the device side and can thus be replaced if necessary.

Figure 2:
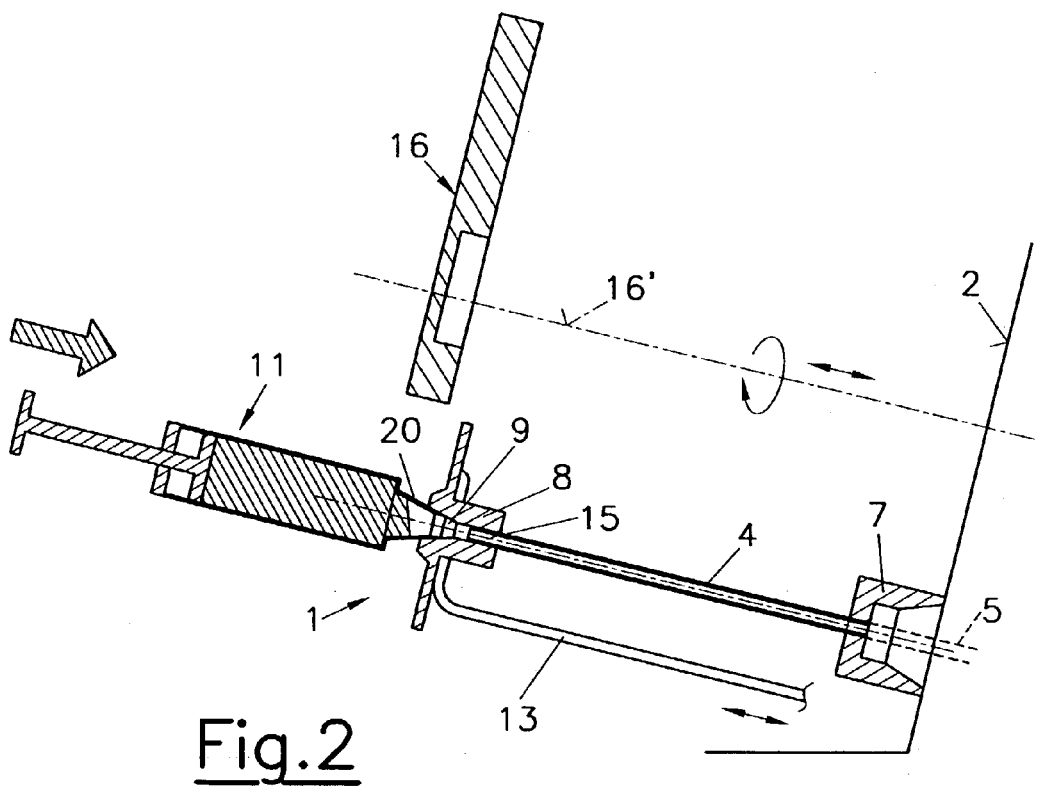

The intake needle 4 carries an axially slideable, elastic intake element 8 with a conical intake opening 9, the conical intake opening 9 being suitable for the sealed insertion of a sample capillary 10 (see FIG. 1) as well as for holding the cone of a syringe 11 (see FIG. 2). Axial shifting of the intake element 8 is performed via an actuating element 13 by a drive unit 12 contained in the analyzer 3 and controlled by a processor unit 14. The axial shift of the elastic intake element 8 takes place between a first position (see FIGS. 1 to 3), in which the intake element 8 is located near the tip 15 of the intake needle 4, and a second position in the middle of the intake needle 4 (see FIG. 4), in which the the tip 15 of the needle projects beyond the intake element 8.

The sample entry device further comprises a holding element 16 which is axially slideable and rotatably pivoted on an axle 16' at a distance r from the intake needle 4, and which in a first rotatory position (FIGS. 1, 2, 5) exposes the intake element 8 for certain types of sample input and which in a second position, rotated by an angle β against the first position (FIGS. 3, 4), places a conical opening 17 in the holding element 16, which holds a syringe 11 in such a way above the elastic intake element 8 that the axis 4' of the rigid intake needle 4 coincides with the axis 17' of the conical opening 17. The lifting and turning motion of the holding element 16 is effected by a further drive unit 18 contained in the analyzer 3 and controlled by the processor unit 14.

The sample entry device according to the invention is thus perfectly suited for the three preferred methods of sample input:

Aspirating the sample from a sample tube of small diameter, e.g., a sample capillary: In this case the device is in the operational state depicted in FIG. 1, i.e., the elastic intake element 8 is located near the tip 15 of the rigid intake needle 4 and the holding element 16 is in its first rotatory position, in which the intake element 8 is exposed for sample input from a sample capillary 10. The sample capillary 10 is now inserted into the conical intake opening 9 of the elastic intake element 8 until it is tightly held in the guiding orifice for the intake needle 4. Thereafter a pumping unit of the analyzer 3 (not shown in the drawing) is activated and the sample is aspirated from the sample capillary into the analyzer. The aspiration process may be initiated manually from a display panel of the analyzer or it may be initiated automatically, for instance by optical scanning means in the area of the intake opening 9 (not shown in the drawing), which may recognize different sample containers by their different diameters.

Injecting the sample from a syringe: This type of sample input is schematically represented in FIG. 2. The sample entry device 1 is in the same initial state as in FIG. 1. In this case the cone 20 of the syringe 11 is tightly inserted into the conical intake opening 9 of the elastic intake element 8 and subsequently the sample contained in the syringe 11 is injected into the analyzer 3 by pressing the plunger 21. The force exerted by the injection process on the axially slideable intake element 8 is taken up by the actuating element 13 of the drive unit 12.

Aspirating the sample from a syringe: This type of sample input is depicted in FIGS. 3 and 4. The sample input device 1 is in an initial position as depicted in FIG. 3, in which the holding element 16 is in its second rotatory position. The conical opening 17 of the holding element 16 is positioned above the intake element 8 in such a way that the axis 4' of the rigid intake needle 4 coincides with the axis 17' of the conical opening 17. Following this the cone 20 of the syringe 11 is inserted into the conical opening of the holding element 16 and held there. Now a lifting motion of the holding element 16 as well as the intake element 8 is initiated, both parts being moved towards the front panel 2 of the analyzer 3 (see FIG. 4). By this lifting motion the syringe 11 is slid over the rigid intake needle 4 and the needle thus penetrates into the interior of the syringe into a bubble-free area of the sample contained in the syringe. As shown in FIGS. 1 to 4 the rigid intake needle 4 is directed slightly upwards at an angle α and the holding element 16 is obliquely directed at the same angle α, such that the syringe 11 is favorably positioned for the bubble-free aspiration of the sample from the syringe. Between the intake element 8 and the holding element 16 ambient air may flow through an annular gap between intake needle 4 and cone 20 into the syringe 11 avoiding the development of a partial vacuum during sample intake. The lifting and rotatory motions required for this type of sample entry may either be initiated manually from a display of the analyzer (preferably a touch screen) or may be initiated automatically by an optical or mechanical recognition device for the sample container used (not shown in the drawings).

Figure 5:
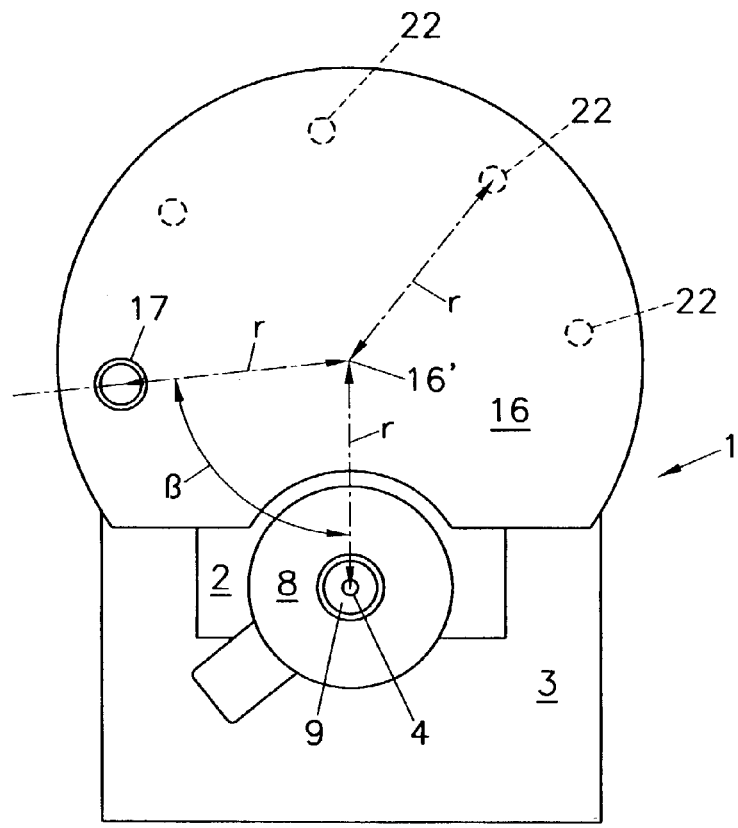
FIG. 5 is a view from above of the sample entry device of FIGS. 1 to 4.

As indicated in FIGS. 3 and 5, respectively, the holding element 16 may be configured as a distributor disk for the supply of calibrating, quality control and/or cleaning media, with fittings 22 being placed at a distance r from the rotation axis 16' in additional positions on the underside of the distributor disk 16. By a suitable lifting and turning motion each of these fittings 22 may be inserted into the elastic intake element 8 and the respective calibrating, quality control and/or cleaning medium may be aspirated into the intake needle 4.

Figure 6:
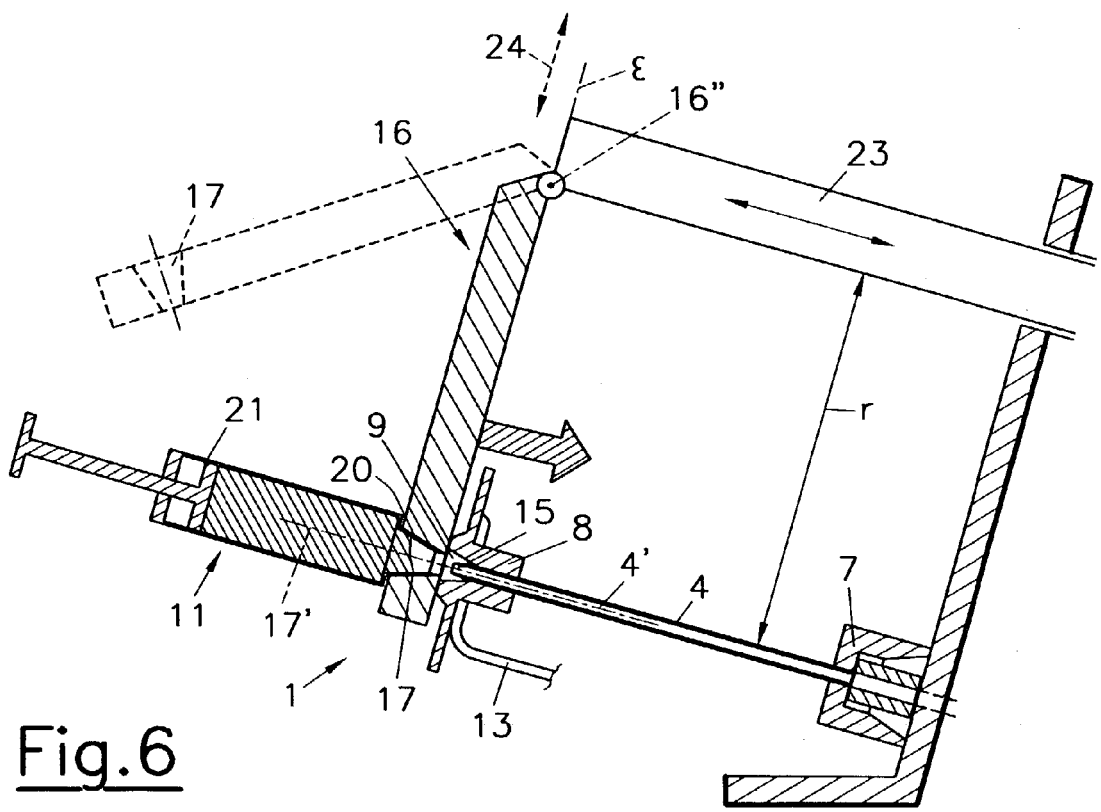
FIG. 6 is a further variant of the invention in a sectional view as in FIG. 3.

In the variant of the invention shown in FIG. 6 the holding element 16 is configured as a flap hinged on one side. The rotation axis 16" is situated in a normal plane ε of the intake needle 4 at a distance r and pivots the flap on a supporting element 23 performing the lifting motion necessary to slide the syringe 11 over the rigid intake needle 4. In a first position of the holding element 16 (broken lines) the intake element 8 for sample input, for instance from a capillary, is exposed; in a second position the conical opening 17 of the flap is placed above the intake element 8 in order to accept a syringe 11.

As indicated by an arrow 24 in FIG. 6, a further variant of the invention may provide that the holding element 16 be brought by translatory motion from a first position (intake element 8 exposed) into a second position (conical opening 17 above the intake element 8), whereupon a lifting motion may be carried out by means of the supporting element 23.

In this way it is ensured that the sample as well as all calibrating, quality control and/or cleaning media will follow the same path of analysis for all of the preferred types of sample entry.

What is claimed is:

1. A sample entry device for delivering medical samples from diverse sample containers to an analyzer, said sample entry device comprising, a fixed intake needle provided at an entry side of said analyzer, an elastic intake element that is slideable along a longitudinal axis of said intake needle, said intake element including a conical intake opening, and a holding element including a conical opening and slideable along an axis parallel to said longitudinal axis of said intake needle and shiftable relative to said intake element, wherein said holding element has a first position in which said elastic intake element is exposed and a second position in which the conical opening is placed above said conical intake opening of said elastic intake element to accommodate a syringe.

2. The sample entry device according to claim 1, wherein said holding element is rotatably pivoted on an axle running parallel to said intake needle at a distance r, such that in a first rotational position said intake element is exposed while in a second rotational position said conical opening is positioned above the intake element.

3. The sample entry device according to claim 2, wherein said holding element is configured as a distributor disk for supply of at least one medium of a group consisting of calibrating, quality control and cleaning media, having fittings for said media being provided in further rotational positions of said distributor disk at a distance r, wherein said fittings can be brought into contact with said intake element.

4. The sample entry device according to claim 1, wherein said holding element is configured as a flap and is rotatably pivoted on an axle situated in a plane orthogonal to said intake needle, such that in a first position of said flap said intake element is exposed while in a second position of said flap said conical opening is positioned above said intake element.

5. An analyzer comprising the sample entry device according to claim 2, and a driving unit for lifting and rotatory motions of said holding element, wherein said driving unit is controlled by a processor unit of said analyzer.

6. An analyzer comprising the sample entry device according to claim 2, and a driving unit for lifting and tilting motions of said holding element, wherein said driving unit is controlled by a processor unit of said analyzer.

7. An analyzer comprising the sample entry device according to claim 1, and a driving unit controlled by a processor unit of said analyzer used for axial shifting of said elastic intake element from a first position near a tip of the intake needle to a second position in which said needle tip projects beyond said intake element, wherein said driving unit is coupled to said elastic intake element via a linking element.

8. An analyzer comprising the sample entry device according to claim 1, and gas-tight sample lines for sample transfer between sample intake and measuring cells of said analyzer.

* * * * *